United States Patent
Murakami (10) Patent No.: US 12,383,227 B2
(45) Date of Patent: Aug. 12, 2025

(54) ULTRASOUND DIAGNOSTIC APPARATUS IN WHICH AN ULTRASOUND PROBE IS USED BY SWITCHING BETWEEN A WIRELESS CONNECTION MODE AND A WIRED CONNECTION MODE WITH RESPECT TO AN APPARATUS MAIN BODY AND A CONTROL METHOD THEREFOR

(71) Applicant: FUJIFILM Corporation, Tokyo (JP)

(72) Inventor: Hiroshi Murakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 67 days.

(21) Appl. No.: 18/365,550

(22) Filed: Aug. 4, 2023

(65) Prior Publication Data

US 2023/0371926 A1 Nov. 23, 2023

Related U.S. Application Data (63) Continuation of application No. PCT/JP2021/045085, filed on Dec. 8, 2021.

(30) Foreign Application Priority Data

Mar. 22, 2021 (JP) .................. 2021-047208

(51) Int. Cl.
*A61B 8/00* (2006.01)

(52) U.S. Cl.
CPC .......... *A61B 8/4472* (2013.01); *A61B 8/4488* (2013.01); *A61B 8/54* (2013.01); *A61B 8/56* (2013.01)

(58) Field of Classification Search
CPC ................. A61B 8/56; A61B 8/4472
See application file for complete search history.

(56) References Cited

U.S. PATENT DOCUMENTS

| 2010/0185096 A1* | 7/2010 | Miyachi | A61B 8/4472 600/459 |
| 2010/0249600 A1* | 9/2010 | Kudoh | A61B 8/565 600/459 |

(Continued)

FOREIGN PATENT DOCUMENTS

| JP | 2011-072467 A | 4/2011 |
| JP | 2019-187783 A | 10/2019 |

OTHER PUBLICATIONS

LTC4412; LT 0215 Rev B; Linear Technology Corporation; 2002; pp. 1-14.

(Continued)

*Primary Examiner* — Pascal M Bui Pho
*Assistant Examiner* — Nyrobi Celestine
(74) *Attorney, Agent, or Firm* — Studebaker Brackett PLLC (57) ABSTRACT

An ultrasound diagnostic apparatus includes an apparatus main body and an ultrasound probe that is used by switching between a wireless connection mode and a wired connection mode with respect to the apparatus main body, the apparatus main body having a main body-side first power supply circuit that generates a main body-side driving voltage and a main body-side second power supply circuit that generates a main body-side transmission voltage higher than the main body-side driving voltage, the ultrasound probe having a transducer array, a built-in battery, a prove-side first power supply circuit that generates a prove-side driving voltage using an output voltage of the built-in battery, a prove-side second power supply circuit that boosts the output voltage of the built-in battery to generate a prove-side transmission voltage higher than the prove-side driving voltage, and a probe side processor.

16 Claims, 6 Drawing Sheets

(56) References Cited

U.S. PATENT DOCUMENTS

| | | | | |
|---|---|---|---|---|
| 2011/0245677 A1* | 10/2011 | Sato | ................... | G01S 7/52079 |
| | | | | 600/447 |
| 2012/0101389 A1* | 4/2012 | Tanabe | ................. | A61B 8/4438 |
| | | | | 600/459 |
| 2012/0197124 A1* | 8/2012 | Nakamura | ............... | A61B 8/42 |
| | | | | 600/443 |
| 2014/0194739 A1* | 7/2014 | Katou | ..................... | A61B 8/56 |
| | | | | 600/447 |
| 2014/0275844 A1* | 9/2014 | Hoseit | .................... | A61B 8/12 |
| | | | | 600/407 |
| 2014/0323861 A1* | 10/2014 | Jin | ....................... | H02J 7/0048 |
| | | | | 367/137 |
| 2019/0059738 A1* | 2/2019 | Suzuki | .............. | G01N 29/2418 |

OTHER PUBLICATIONS

International Search Report issued in PCT/JP2021/045085; mailed Mar. 8, 2022.

International Preliminary Report on Patentability (Chapter I) and Written Opinion of the International Searching Authority issued in PCT/JP2021/045085; issued Sep. 12, 2023.

* cited by examiner

ULTRASOUND DIAGNOSTIC APPARATUS IN WHICH AN ULTRASOUND PROBE IS USED BY SWITCHING BETWEEN A WIRELESS CONNECTION MODE AND A WIRED CONNECTION MODE WITH RESPECT TO AN APPARATUS MAIN BODY AND A CONTROL METHOD THEREFOR

CROSS-REFERENCE TO RELATED APPLICATIONS

This application is a Continuation of PCT International Application No. PCT/JP2021/045085 filed on Dec. 8, 2021, which claims priority under 35 U.S.C. § 119(a) to Japanese Patent Application No. 2021-047208 filed on Mar. 22, 2021. The above applications are hereby expressly incorporated by reference, in their entirety, into the present application.

BACKGROUND OF THE INVENTION

1. Field of the Invention

The present invention relates to an ultrasound diagnostic apparatus and a control method for an ultrasound diagnostic apparatus, and particularly, to an ultrasound diagnostic apparatus and a control method for an ultrasound diagnostic apparatus for switching and using two connection modes: wired connection and wireless connection, between an ultrasound probe and an apparatus main body.

2. Description of the Related Art

Hitherto, in the medical field, an ultrasound diagnostic apparatus using an ultrasound image has been put to practical use. In general, this type of ultrasound diagnostic apparatus comprises an ultrasound probe incorporating a transducer array, and an apparatus main body connected to the ultrasound probe, and an ultrasound beam is transmitted from the transducer array of the ultrasound probe toward a subject under examination, an ultrasound echo from the subject under examination is received by the transducer array, and a reception signal is electrically processed, so that an ultrasound image is generated and displayed on a monitor of the apparatus main body.

In recent years, an ultrasound diagnostic apparatus has been developed to improve operability and mobility of an ultrasound probe by establishing a wireless connection between the ultrasound probe and an apparatus main body through wireless communication.

Further, for example, JP2019-187783A discloses an ultrasound diagnostic apparatus that switches and uses two connection modes: wired connection and wireless connection, between an ultrasound probe and an apparatus main body such that one of wired connection or wireless connection can be selected.

SUMMARY OF THE INVENTION

An ultrasound probe that can be wirelessly connected to an apparatus main body, such as the ultrasound probe in JP2019-187783A, often incorporates all circuits from transmission and reception of ultrasound waves to generation of an ultrasound image, and both during wireless connection and during wired connection, each circuit in the ultrasound probe operates in the same operational environment.

However, in the ultrasound probe that can be wirelessly connected, each circuit is accommodated within a limited space inside a housing. This requires balancing factors such as heat generation, battery voltage, and wireless bandwidth for each circuit. As a result, constraints have inevitably been imposed on the transmission voltage for transmitting ultrasound waves from a transducer array, a frame rate for generating ultrasound images, a usage time of the ultrasound probe, and the like.

Therefore, it is desired to realize higher performance for the ultrasound probe that can be wirelessly connected.

The present invention has been made in order to solve such a conventional problem, and an object of the present invention is to provide an ultrasound diagnostic apparatus and a control method for an ultrasound diagnostic apparatus capable of improving a performance thereof even in a case of switching and using two connection modes: wired connection and wireless connection, between an ultrasound probe and an apparatus main body.

In order to achieve the above-described object, according to the present invention, there is provided an ultrasound diagnostic apparatus comprising:

an apparatus main body; and
an ultrasound probe that is used by switching between a wireless connection mode and a wired connection mode with respect to the apparatus main body,
in which the apparatus main body includes an external power supply circuit, and
the ultrasound probe includes
a transducer array,
a transmission circuit configured to transmit an ultrasound wave toward a subject under examination by supplying a transmission voltage to the transducer array,
a reception circuit configured to receive an ultrasound echo from the subject under examination and acquire a reception signal,
a built-in battery,
an in-probe power supply circuit configured to generate the transmission voltage using an output voltage of the built-in battery, and
a probe control unit configured to supply the transmission voltage from the in-probe power supply circuit to the transmission circuit in a case where the apparatus main body is connected to the ultrasound probe via wireless connection, and to supply the transmission voltage from the external power supply circuit of the apparatus main body to the transmission circuit in a case where the apparatus main body is connected to the ultrasound probe via wired connection.

It is preferable that, in a case where the apparatus main body is connected to the ultrasound probe via wired connection, a transmission voltage higher than the transmission voltage supplied from the in-probe power supply circuit during wireless connection is supplied from the external power supply circuit of the apparatus main body to the transmission circuit.

The probe control unit may be configured to: drive the reception circuit in a low power consumption mode in a case where the apparatus main body is connected to the ultrasound probe via wireless connection; and drive the reception circuit in a low noise mode in a case where the apparatus main body is connected to the ultrasound probe via wired connection.

In addition, the ultrasound probe may include an image generation unit configured to generate an ultrasound image based on the reception signal, and the probe control unit may be configured to supply power from the external power supply circuit of the apparatus main body to the transmission circuit, the reception circuit, and the image generation unit in a case where the apparatus main body is connected to the ultrasound probe via wired connection, and to cause the image generation unit to generate the ultrasound image at a higher frame rate than a frame rate during wireless connection.

A configuration may also be employed in which, in a case where the apparatus main body is connected to the ultrasound probe via wireless connection, a variable transmission voltage is supplied from the in-probe power supply circuit to the transmission circuit, and in a case where the apparatus main body is connected to the ultrasound probe via wired connection, a variable transmission voltage having a voltage range wider than a voltage range of the transmission voltage during wireless connection is supplied from the external power supply circuit of the apparatus main body to the transmission circuit.

The ultrasound probe may include a booster circuit configured to boost the output voltage of the built-in battery, and the in-probe power supply circuit may be configured to generate the transmission voltage using an output voltage of the booster circuit.

According to the present invention, there is provided a control method for an ultrasound diagnostic apparatus including an apparatus main body that includes an external power supply circuit, and an ultrasound probe that is used by switching between a wireless connection mode and a wired connection mode with respect to the apparatus main body and that includes a transducer array, a transmission circuit, a reception circuit, and a built-in battery, the control method comprising:

supplying a transmission voltage from an in-probe power supply circuit, which is configured to generate the transmission voltage using an output voltage of the built-in battery, to the transmission circuit in a case where the apparatus main body is connected to the ultrasound probe via wireless connection; and supplying the transmission voltage from the external power supply circuit of the apparatus main body to the transmission circuit in a case where the apparatus main body is connected to the ultrasound probe via wired connection.

It is preferable that, in a case where the apparatus main body is connected to the ultrasound probe via wired connection, a transmission voltage higher than the transmission voltage supplied from the in-probe power supply circuit during wireless connection is supplied from the external power supply circuit of the apparatus main body to the transmission circuit.

The reception circuit may be driven in a low power consumption mode in a case where the apparatus main body is connected to the ultrasound probe via wireless connection, and the reception circuit may be driven in a low noise mode in a case where the apparatus main body is connected to the ultrasound probe via wired connection.

The ultrasound probe may include an image generation unit configured to generate an ultrasound image based on the reception signal, and power may be supplied from the external power supply circuit of the apparatus main body to the transmission circuit, the reception circuit, and the image generation unit in a case where the apparatus main body is connected to the ultrasound probe via wired connection, and the ultrasound image may be generated by the image generation unit at a higher frame rate than a frame rate during wireless connection.

A configuration may also be employed in which, in a case where the apparatus main body is connected to the ultrasound probe via wireless connection, a variable transmission voltage is supplied from the in-probe power supply circuit to the transmission circuit, and in a case where the apparatus main body is connected to the ultrasound probe via wired connection, a variable transmission voltage having a voltage range wider than a voltage range of the transmission voltage during wireless connection is supplied from the external power supply circuit of the apparatus main body to the transmission circuit.

According to the present invention, in a case where the apparatus main body is connected to the ultrasound probe via wireless connection, a transmission voltage is supplied from the in-probe power supply circuit, which generates the transmission voltage using the output voltage of the built-in battery of the ultrasound probe, to the transmission circuit, and in a case where the apparatus main body is connected to the ultrasound probe via wired connection, the transmission voltage is supplied from the external power supply circuit of the apparatus main body to the transmission circuit. Therefore, it is possible to improve the performance even in a case of switching and using two connection modes: wired connection and wireless connection, between the ultrasound probe and the apparatus main body.

DESCRIPTION OF THE PREFERRED EMBODIMENTS

Hereinafter, an embodiment of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment 1

Figure 1:
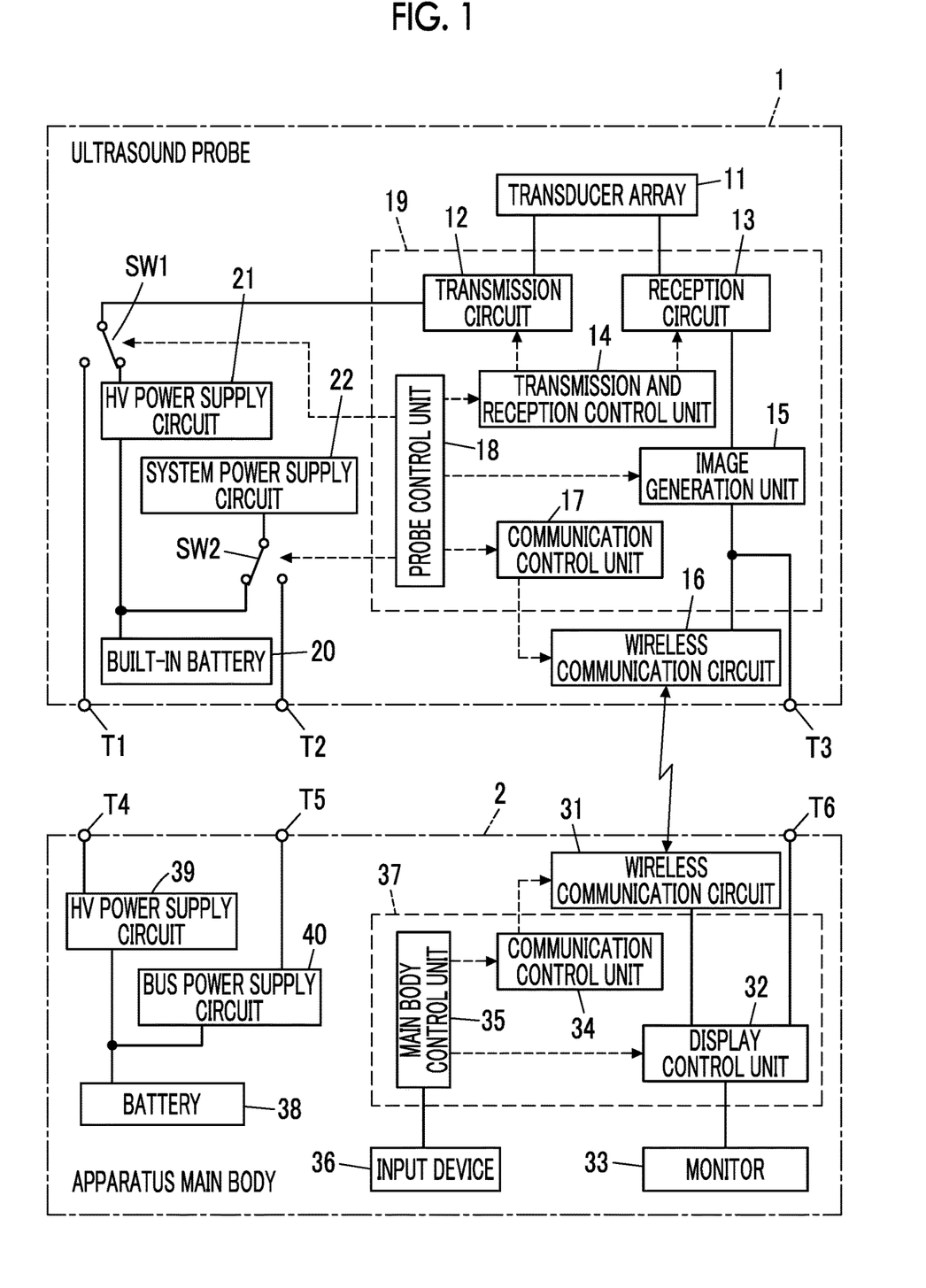
FIG. 1 is a block diagram showing a configuration of an ultrasound diagnostic apparatus according to Embodiment 1 of the present invention during wireless connection.

FIG. 1 shows a configuration of an ultrasound diagnostic apparatus according to Embodiment 1 of the present invention. The ultrasound diagnostic apparatus is an ultrasound diagnostic apparatus that includes an ultrasound probe 1 and an apparatus main body 2 connected to the ultrasound probe 1 and that switches and uses two connection modes: wired connection and wireless connection, between the ultrasound probe 1 and the apparatus main body 2.

As shown in FIG. 1, the ultrasound probe 1 includes a transducer array 11, and a transmission circuit 12 and a reception circuit 13 are connected to the transducer array 11. A transmission and reception control unit 14 is connected to the transmission circuit 12 and the reception circuit 13, and an image generation unit 15 is connected to the reception circuit 13. A wireless communication circuit 16 is connected to the image generation unit 15, and a communication control unit 17 is further connected to the wireless communication circuit 16.

The probe control unit 18 is connected to the transmission and reception control unit 14, the image generation unit 15, and the communication control unit 17.

A probe side processor 19 is composed of the transmission circuit 12, the reception circuit 13, the transmission and reception control unit 14, the image generation unit 15, the communication control unit 17, and the probe control unit 18.

In addition, the ultrasound probe 1 incorporates a built-in battery 20, and a high voltage (HV) power supply circuit (in-probe power supply circuit) 21 and a system power supply circuit 22 are each connected to the built-in battery 20. Further, the ultrasound probe 1 includes connection terminals T1, T2, and T3 for connecting the ultrasound probe 1 to the apparatus main body 2 via a connection cable (not shown), and a first changeover switch SW1 is connected between the HV power supply circuit 21 and the connection terminal T1, and the transmission circuit 12, a second changeover switch SW2 is connected between the built-in battery 20 and the connection terminal T2, and the system power supply circuit 22, and the image generation unit 15 is connected to the connection terminal T3.

Meanwhile, the apparatus main body 2 includes a wireless communication circuit 31, and a display control unit 32 and a monitor 33 are sequentially connected to the wireless communication circuit 31. In addition, a communication control unit 34 is connected to the wireless communication circuit 31, and a main body control unit 35 is connected to the display control unit 32 and the communication control unit 34. Further, an input device 36 is connected to the main body control unit 35.

A main body side processor 37 is composed of the display control unit 32, the communication control unit 34, and the main body control unit 35.

In addition, the apparatus main body 2 incorporates a battery 38, and a high voltage (HV) power supply circuit 39 and a bus power supply circuit 40 are each connected to the battery 38. The HV power supply circuit 39 and the bus power supply circuit 40 constitute an external power supply circuit disposed outside the ultrasound probe 1. Further, the apparatus main body 2 includes connection terminals T4, T5, and T6 for connecting the apparatus main body 2 to the ultrasound probe 1 via the connection cable (not shown), and the HV power supply circuit 39 is connected to the connection terminal T4, the bus power supply circuit 40 is connected to the connection terminal T5, and the display control unit 32 is connected to the connection terminal T6.

The transducer array 11 of the ultrasound probe 1 includes a plurality of ultrasound transducers one-dimensionally or two-dimensionally arranged. Each of these transducers transmits an ultrasound wave in accordance with a drive signal supplied from the transmission circuit 12 and outputs an analog reception signal by receiving a reflected wave from the subject under examination. For example, each transducer is composed of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like, and electrodes formed at both ends of the piezoelectric body.

The transmission circuit 12 includes, for example, a plurality of pulse generators and supplies respective drive signals to the plurality of transducers by adjusting delay amounts such that ultrasound waves transmitted from the plurality of transducers of the transducer array 11 form an ultrasound beam, based on a transmission delay pattern selected according to a control signal from the transmission and reception control unit 14. In this way, in a case where a pulsed or continuous-wave voltage is applied to the electrodes of the transducer of the transducer array 11, the piezoelectric body expands and contracts, and a pulsed or continuous-wave ultrasound wave is generated from each of the transducers, so that the ultrasound beam is formed from a combined wave of these ultrasound waves.

The transmitted ultrasound beam is reflected in, for example, a target such as a site of the subject under examination, and an ultrasound echo propagates toward the transducer array 11. The ultrasound echo propagating toward the transducer array 11 in this way is received by each of the transducers constituting the transducer array 11. At this time, each of the transducers constituting the transducer array 11 expands and contracts by receiving the propagating ultrasound echo, and generates a reception signal (electrical signal), thereby outputting these reception signals to the reception circuit 13.

Figure 2:
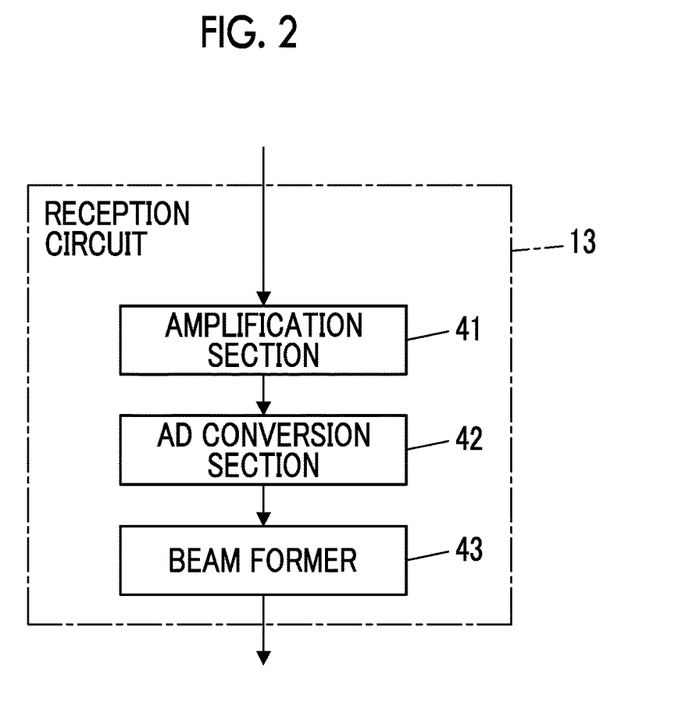
FIG. 2 is a block diagram showing an internal configuration of a reception circuit in Embodiment 1.

The reception circuit 13 processes the signals output from the transducer array 11 in accordance with a control signal from the transmission and reception control unit 14 to generate a sound ray signal. As shown in FIG. 2, the reception circuit 13 has a configuration in which an amplification section 41, an analog-to-digital (AD) conversion section 42, and a beam former 43 are connected in series.

The amplification section 41 amplifies the reception signal, which is an analog signal input from each of the transducers constituting the transducer array 11, and transmits the amplified reception signal to the AD conversion section 42.

The AD conversion section 42 converts the analog reception signal transmitted from the amplification section 41 into a digital signal to acquire reception data and sends out the reception data to the beam former 43.

The beam former 43 performs so-called reception focus processing of performing addition (phase addition) by applying a delay to each reception data following a set sound velocity based on a reception delay pattern selected according to a control signal from the transmission and reception control unit 14. By performing this reception focus processing, a sound ray signal in which the focus of the ultrasound echo is narrowed down is generated.

The transmission and reception control unit 14 controls the transmission circuit 12 and the reception circuit 13 to transmit the ultrasound beam and receive the ultrasound echo based on an examination mode and a scanning method as instructed by the probe control unit 18. Here, the examination mode includes available examination modes in the ultrasound diagnostic apparatus, such as a brightness mode (B-mode), a motion mode (M-mode), a color flow mode (CF-mode), a pulsed wave doppler mode (PW-mode), and a continuous wave doppler mode (CW-mode), and the scanning method indicates, for example, any one of an electronic sector scanning method, an electronic linear scanning method, an electronic convex scanning method, or the like.

Figure 3:
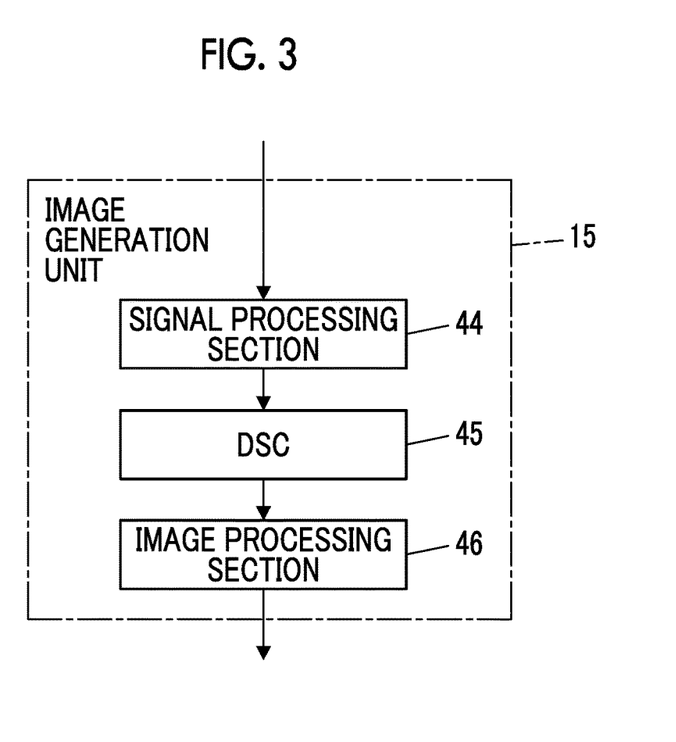
FIG. 3 is a block diagram showing an internal configuration of an image generation unit in Embodiment 1.

The image generation unit 15 generates a so-called B-mode image based on the sound ray signal generated by the reception circuit 13. As shown in FIG. 3, the image generation unit 15 has a configuration in which a signal processing section 44, a digital scan converter (DSC) 45, and an image processing section 46 are sequentially connected in series.

The signal processing section 44 generates a B-mode image signal, which is tomographic image information regarding the internal tissues of the subject under examination, by performing envelope detection processing after correcting the attenuation caused by a distance according to the depth of the position where ultrasound waves are reflected, with respect to the sound ray signal generated by the reception circuit 13.

The DSC 45 converts (raster-converts) the B-mode image signal generated by the signal processing section 44 into an image signal according to a normal television signal scanning method.

The image processing section 46 performs various types of necessary image processing, such as gradation processing, on the B-mode image signal input from the DSC 45 and then sends out the B-mode image signal (hereinafter, referred to as a B-mode image), which has been subjected to image processing, to the wireless communication circuit 16 and the connection terminal T3.

The wireless communication circuit 16 wirelessly transmits the B-mode image generated by the image generation unit 15 to the apparatus main body 2 in a case where the ultrasound probe 1 and the apparatus main body 2 are connected to each other via wireless connection.

More specifically, the wireless communication circuit 16 includes an antenna for transmitting and receiving radio waves, and modulates a carrier based on the B-mode image to generate a transmission signal and supplies the transmission signal to the antenna to transmit the radio waves from the antenna, thereby wirelessly transmitting the B-mode image to the apparatus main body 2. As a carrier modulation method, amplitude shift keying (ASK), phase shift keying (PSK), quadrature phase shift keying (QPSK), 16 quadrature amplitude modulation (16QAM), and the like are used.

The communication control unit 17 controls the wireless communication circuit 16 such that the B-mode image is transmitted at a transmission radio wave intensity set by the probe control unit 18.

The probe control unit 18 controls each unit of the ultrasound probe 1 based on a program or the like stored in advance.

Further, the built-in battery 20 is incorporated into the ultrasound probe 1, is composed of, for example, a single-cell lithium ion battery having an output voltage, such as 3.6 V, and is a battery that allows for a small mounting space within the ultrasound probe 1. The built-in battery 20 supplies the output voltage to the HV power supply circuit 21 and the system power supply circuit 22.

The HV power supply circuit 21 has, for example, a boost converter configuration that does not use a transformer, and is a power supply circuit that is difficult to obtain a relatively high voltage but allows for a small mounting space within the ultrasound probe 1. Specifically, the HV power supply circuit 21 boosts the output voltage from the built-in battery 20 to, for example, 36 V, which is about 10 times, or the like and supplies the boosted voltage to the transmission circuit 12 as the transmission voltage. This transmission voltage is supplied as a drive signal to each of the transducers constituting the transducer array 11 by the transmission circuit 12.

The system power supply circuit 22 converts the output voltage from the built-in battery 20 into, for example, about 1 to 3 V and supplies the converted voltage to each circuit in the ultrasound probe 1 as a drive voltage.

The first changeover switch SW1 is switched and controlled by the probe control unit 18 to selectively connect one of the HV power supply circuit 21 or the connection terminal T1 to the transmission circuit 12.

Similarly, the second changeover switch SW2 is switched and controlled by the probe control unit 18 to selectively connect one of the built-in battery 20 or the connection terminal T2 to the system power supply circuit 22.

As shown in FIG. 1, the probe control unit 18 switches and controls the first changeover switch SW1 such that the HV power supply circuit 21 is connected to the transmission circuit 12, and switches and controls the second changeover switch SW2 such that the built-in battery 20 is connected to the system power supply circuit 22, in a case where the apparatus main body 2 is connected to the ultrasound probe 1 via wireless connection.

Figure 4:
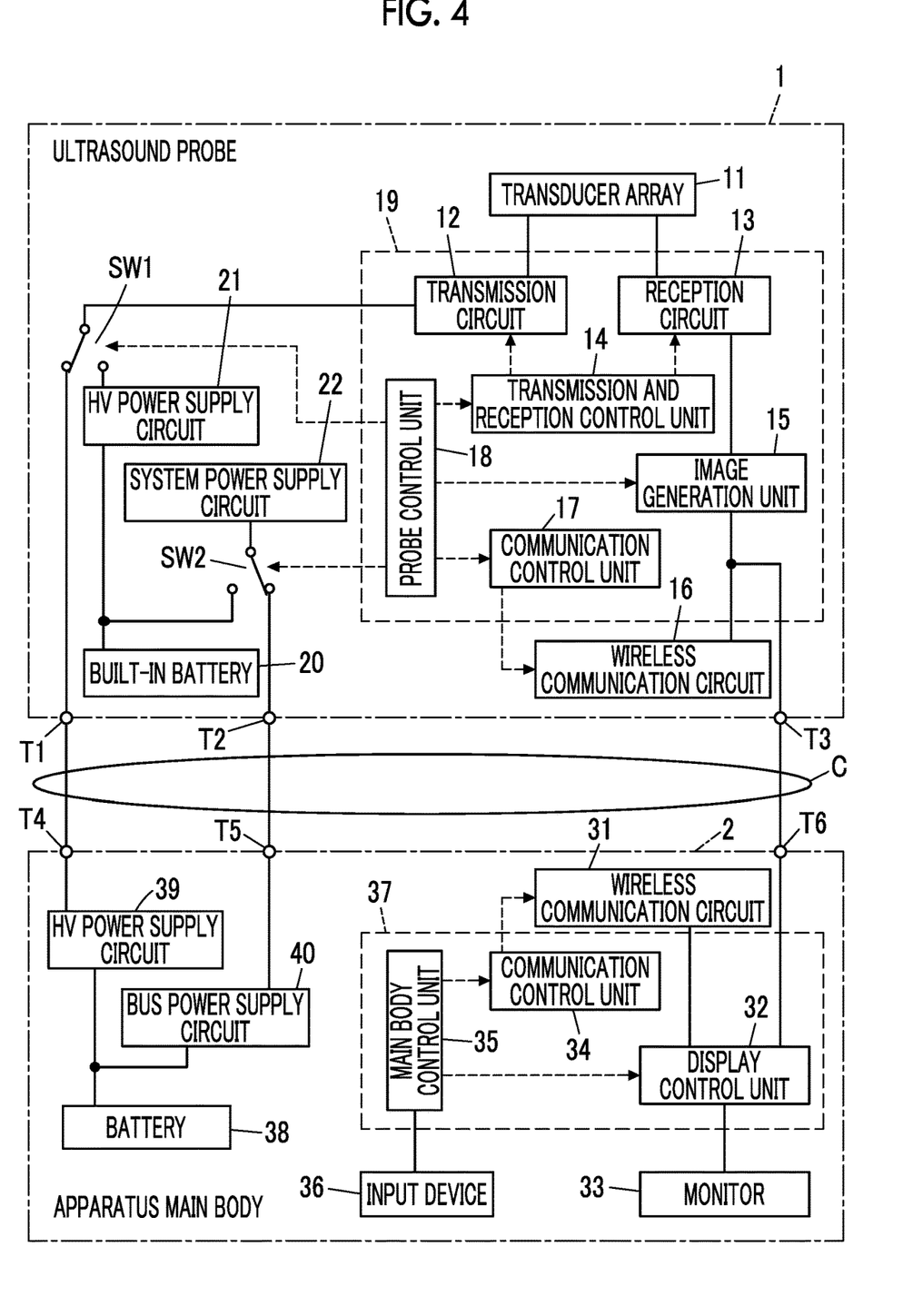
FIG. 4 is a block diagram showing a configuration of the ultrasound diagnostic apparatus according to Embodiment 1 during wired connection.

On the other hand, as shown in FIG. 4, in a case where the apparatus main body 2 is connected to the ultrasound probe 1 via wired connection using a cable C, the probe control unit 18 switches and controls the first changeover switch SW1 such that the connection terminal T1 is connected to the transmission circuit 12, and switches and controls the second changeover switch SW2 such that the connection terminal T2 is connected to the system power supply circuit 22.

The probe side processor 19 including the transmission circuit 12, the reception circuit 13, the transmission and reception control unit 14, the image generation unit 15, the communication control unit 17, and the probe control unit 18 of the ultrasound probe 1 is composed of a central processing unit (CPU) that executes various programs and a control program for causing the CPU to perform various types of processing, but the probe side processor 19 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the transmission circuit 12, the reception circuit 13, the transmission and reception control unit 14, the image generation unit 15, the communication control unit 17, and the probe control unit 18 of the probe side processor 19 can also be configured by being partially or wholly integrated into one CPU or the like.

The wireless communication circuit 31 of the apparatus main body 2 receives the B-mode image wirelessly transmitted from the wireless communication circuit 16 of the ultrasound probe 1.

More specifically, the wireless communication circuit 31 includes an antenna for transmitting and receiving radio waves, and receives a transmission signal transmitted by the wireless communication circuit 16 of the ultrasound probe 1 via the antenna and demodulates the received transmission signal to send out the B-mode image to the display control unit 32.

The display control unit 32 causes the monitor 33 to display the B-mode image received via the wireless communication circuit 31 as a display image.

The monitor 33 is controlled by the display control unit 32 to display the B-mode image as the display image, and examples thereof include a display device, such as a liquid crystal display (LCD) and an organic electroluminescence display (organic EL display).

The communication control unit 34 controls the wireless communication circuit 31 such that the transmission signal transmitted from the wireless communication circuit 16 of the ultrasound probe 1 is received.

The main body control unit 35 controls each unit of the apparatus main body 2 based on a program stored in advance in a storage unit (not shown) or the like and an input operation performed by an operator via the input device 36.

The input device 36 is used for the operator to perform an input operation, and can be configured by a keyboard, a mouse, a trackball, a touch pad, a touch panel, or the like. A configuration can also be employed in which a touch sensor is combined with the monitor 33 and the touch sensor is used as the input device 36.

The battery 38 supplies power to the HV power supply circuit 39 and the bus power supply circuit 40. For example, the battery 38 is composed of a plurality of cells of lithium ion batteries connected in series.

The HV power supply circuit 39 has, for example, a flyback converter configuration using a transformer and is a power supply circuit that requires a large mounting space but can obtain a higher voltage. Specifically, the HV power supply circuit 39 boosts an output voltage from the battery 38 to about 70 to 100 V and supplies the transmission voltage to the transmission circuit 12 of the ultrasound probe 1 via the cable C in a case where the apparatus main body 2 is connected to the ultrasound probe 1 via wired connection using the cable C. That is, a transmission voltage higher than the transmission voltage supplied by the HV power supply circuit 21 in the ultrasound probe 1 can be supplied from the HV power supply circuit 39 of the apparatus main body 2 to the transmission circuit 12 of the ultrasound probe 1 during wired connection.

The bus power supply circuit 40 converts the output voltage from the battery 38 to, for example, about 5 V and supplies the converted voltage as a drive voltage to each circuit in the apparatus main body 2, and supplies power to the system power supply circuit 22 of the ultrasound probe 1 via the cable (not shown) in a case where the apparatus main body 2 is connected to the ultrasound probe 1 via wired connection.

The main body side processor 37 including the display control unit 32, the communication control unit 34, and the main body control unit 35 of the apparatus main body 2 is composed of a CPU and a control program for causing the CPU to perform various types of processing, but the main body side processor 37 may be composed of FPGA, DSP, ASIC, GPU, or other ICs, or may be composed of a combination thereof.

In addition, the display control unit 32, the communication control unit 34, and the main body control unit 35 of the main body side processor 37 can also be configured by being partially or wholly integrated into one CPU or the like.

Next, the operation of the ultrasound diagnostic apparatus according to Embodiment 1 will be described with reference to the flowchart of FIG. 5.

First, in step S1, it is determined whether the ultrasound probe 1 and the apparatus main body 2 are connected via wireless connection or via wired connection. This determination can be performed, for example, by the probe control unit 18 of the ultrasound probe 1 monitoring potentials of the connection terminals T1 and T2, or monitoring the communication environment in the wireless communication circuit 16.

As a result of the determination, as shown in FIG. 1, in a case where the ultrasound probe 1 and the apparatus main body 2 are connected via wireless connection, the process proceeds to step S2, and the transmission voltage for transmitting ultrasound waves is supplied from the built-in battery 20 of the ultrasound probe 1 to the transmission circuit 12. Specifically, the first changeover switch SW1 is switched and controlled by the probe control unit 18 such that the HV power supply circuit 21 is connected to the transmission circuit 12, and the HV power supply circuit 21 boosts the output voltage from the built-in battery 20 to, for example, 36 V or the like and supplies the boosted voltage to the transmission circuit 12 via the first changeover switch SW1.

In addition, the second changeover switch SW2 is switched and controlled by the probe control unit 18 such that the built-in battery 20 is connected to the system power supply circuit 22. As a result, the system power supply circuit 22 converts the output voltage from the built-in battery 20 into, for example, about 1 to 3 V and supplies the converted voltage to each circuit in the ultrasound probe 1 as the drive voltage.

In the apparatus main body 2, the bus power supply circuit 40 converts the output voltage from the battery 38 into, for example, about 5 V and supplies the converted voltage to each circuit in the apparatus main body 2 as the drive voltage.

Figure 6:
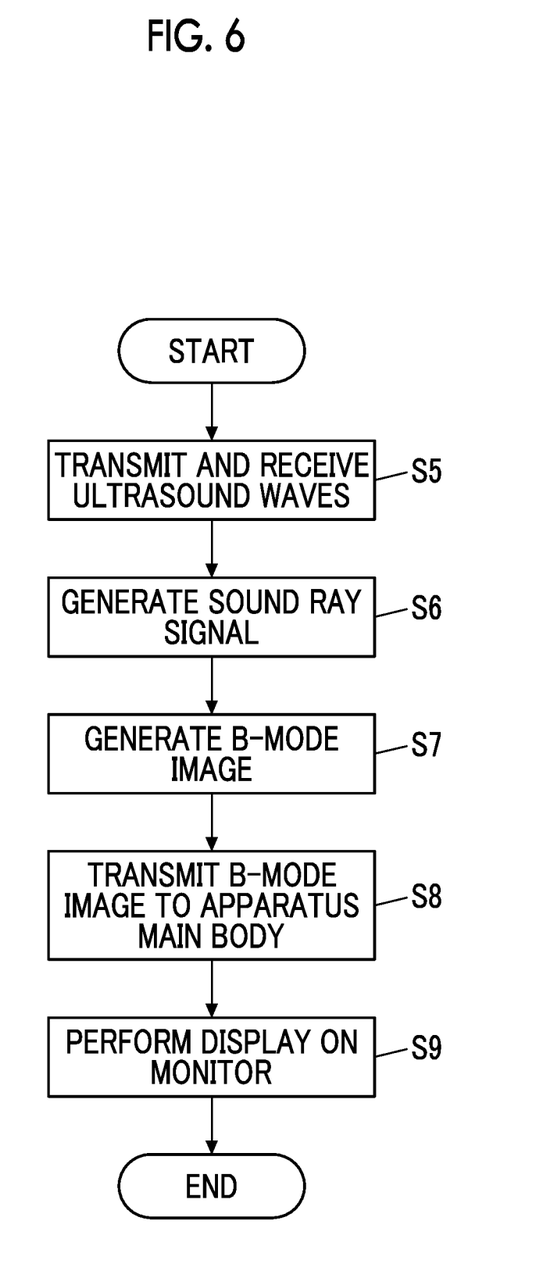
FIG. 6 is a flowchart showing an operation of the ultrasound diagnostic apparatus in a case of performing an ultrasound examination.

In a case of performing examination using ultrasound waves, as shown in the flowchart of FIG. 6, first, in step S5, the ultrasound beam is transmitted into the subject under examination from the plurality of transducers of the transducer array 11 in accordance with the drive signal from the transmission circuit 12 under the control of the transmission and reception control unit 14 of the ultrasound probe 1. Here, the drive signal supplied from the transmission circuit 12 to the plurality of transducers of the transducer array 11 is formed based on the transmission voltage supplied from the HV power supply circuit 21 to the transmission circuit 12.

The ultrasound echo by the subject under examination is received by the plurality of transducers of the transducer array 11, and the reception signal, which is an analog signal, is output from the plurality of transducers to the reception circuit 13.

In subsequent step S6, the reception signal is amplified by the amplification section 41 of the reception circuit 13, subjected to AD conversion by the AD conversion section 42, and then subjected to reception focus processing by the beam former 43, whereby the sound ray signal is generated, and the sound ray signal is sent out from the reception circuit 13 to the image generation unit 15.

Further, in step S7, the B-mode image is generated by the image generation unit 15 based on the sound ray signal.

At this time, the B-mode image signal is generated by correcting the attenuation caused by the distance according to the depth of the position where ultrasound waves are reflected and performing the envelope detection processing through the signal processing section 44 of the image generation unit 15, the B-mode image signal is converted into the image signal according to the normal television signal scanning method by the DSC 45, and various types of necessary image processing, such as gradation processing, is performed by the image processing section 46, so that the B-mode image is generated.

The B-mode image generated in this manner is transmitted from the ultrasound probe 1 to the apparatus main body 2 in step S8. At this time, since the ultrasound probe 1 is connected to the apparatus main body 2 via wireless connection, the B-mode image generated by the image generation unit 15 is wirelessly transmitted from the wireless communication circuit 16 to the apparatus main body 2.

The B-mode image wirelessly transmitted from the ultrasound probe 1 to the apparatus main body 2 is received by the wireless communication circuit 31 of the apparatus main body 2 and displayed on the monitor 33 via the display control unit 32 in step S9.

Figure 5:
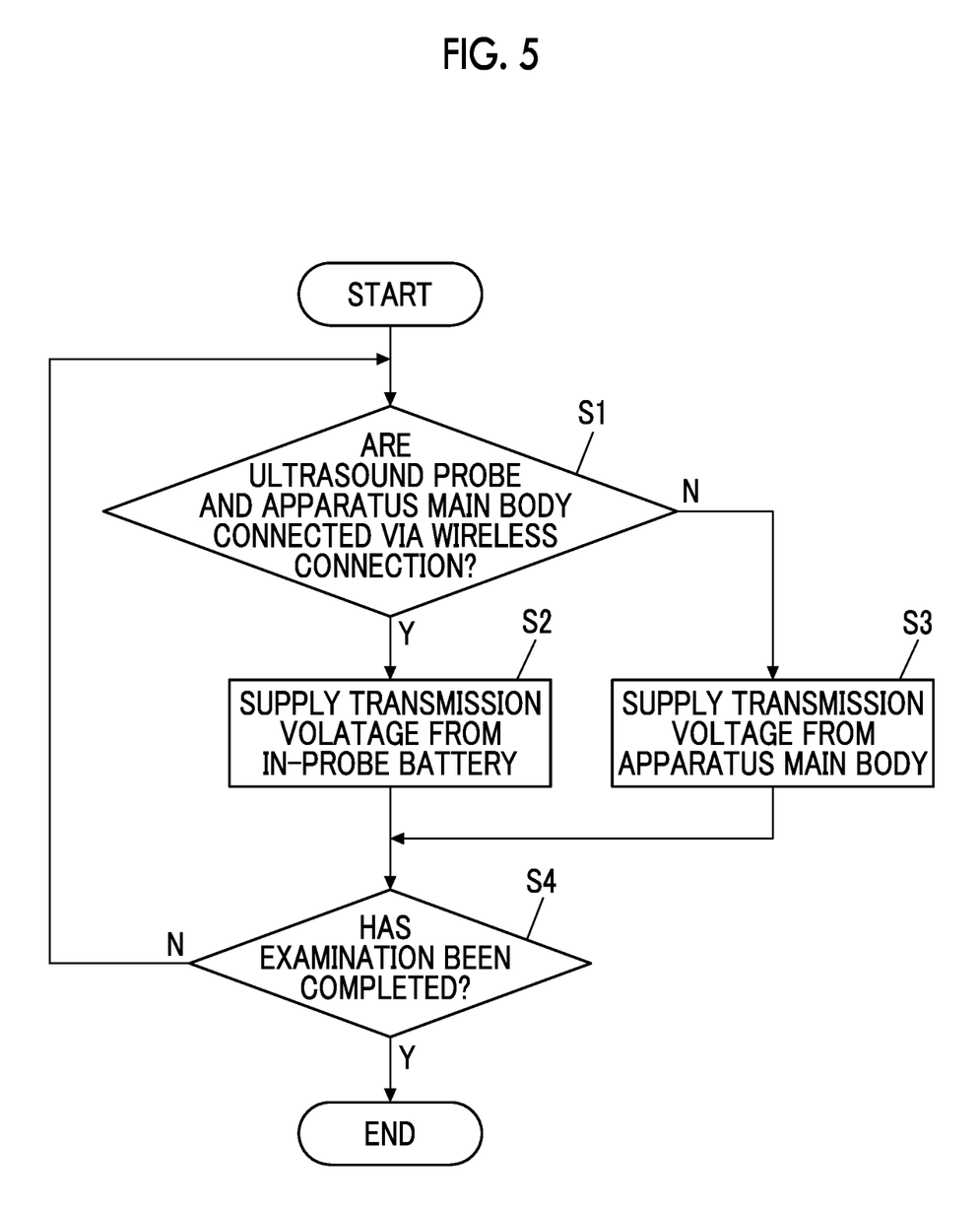
FIG. 5 is a flowchart showing an operation of the ultrasound diagnostic apparatus according to Embodiment 1.

After that, in step S4 of FIG. 5, it is determined whether or not the examination using ultrasound waves has been completed, and in a case where it is determined that the examination has not yet been completed, the process returns to step S1, and processing of steps S1 and S2 is repeated, and in a case where it is determined that the examination has been completed, a series of processing ends.

On the other hand, as a result of the determination in step S1, as shown in FIG. 4, in a case where the ultrasound probe 1 and the apparatus main body 2 are connected via wired connection using the cable C, the process proceeds to step S3, and the transmission voltage for transmitting ultrasound waves is supplied from the apparatus main body 2 to the transmission circuit 12 of the ultrasound probe 1. Specifically, the first changeover switch SW1 is switched and controlled by the probe control unit 18 such that the connection terminal T1 is connected to the transmission circuit 12, and a power voltage boosted to about 70 to 100 V by the HV power supply circuit 39 of the apparatus main body 2 is supplied to the transmission circuit 12 of the ultrasound probe 1 via the connection terminal T4 of the apparatus main body 2, the cable C, the connection terminal T1 of the ultrasound probe 1, and the first changeover switch SW1.

In addition, the second changeover switch SW2 is switched and controlled by the probe control unit 18 such that the connection terminal T2 is connected to the system power supply circuit 22. As a result, a power voltage converted to, for example, about 5 V by the bus power supply circuit 40 of the apparatus main body 2, which constitutes the external power supply circuit, is supplied to the system power supply circuit 22 of the ultrasound probe 1 via the connection terminal T5 of the apparatus main body 2, the cable C, the connection terminal T2 of the ultrasound probe 1, and the second changeover switch SW2. The system power supply circuit 22 receives the power voltage supplied from the bus power supply circuit 40 of the apparatus main body 2 and supplies the drive voltage to each circuit in the ultrasound probe 1.

In a case of performing examination using ultrasound waves, as shown in the flowchart of FIG. 6, first, in step S5, the ultrasound beam is transmitted into the subject under examination from the plurality of transducers of the transducer array 11 in accordance with the drive signal from the transmission circuit 12 under the control of the transmission and reception control unit 14 of the ultrasound probe 1. Here, the drive signal supplied from the transmission circuit 12 to the plurality of transducers of the transducer array 11 is formed based on the transmission voltage that is boosted to about 70 to 100 V by the HV power supply circuit 39 of the apparatus main body 2, which constitutes the external power supply circuit, and that is supplied to the transmission circuit 12 of the ultrasound probe 1.

That is, a transmission voltage higher than a transmission voltage of 36 V or the like supplied from the HV power supply circuit 21 in the ultrasound probe 1 to the transmission circuit 12 during wireless connection is supplied from the HV power supply circuit 39 of the apparatus main body 2 to the transmission circuit 12 during wired connection. Therefore, a stronger (higher-energy) ultrasound beam can be transmitted from the plurality of transducers of the transducer array 11.

The ultrasound echo by the subject under examination is received by the plurality of transducers of the transducer array 11, and the reception signal, which is an analog signal, is output from the plurality of transducers to the reception circuit 13. Then, in step S6, the sound ray signal is generated by the reception circuit 13, and in step S7, the B-mode image is further generated by the image generation unit 15.

The generated B-mode image is transmitted from the ultrasound probe 1 to the apparatus main body 2 in subsequent step S8. However, since the ultrasound probe 1 is connected to the apparatus main body 2 via wired connection, the B-mode image generated by the image generation unit 15 is transmitted to the apparatus main body 2 via the connection terminal T3 of the ultrasound probe 1, the cable C, and connection terminal T6 of the apparatus main body 2. Then, the B-mode image is displayed on the monitor 33 by the display control unit 32 of the apparatus main body 2.

As described above, a stronger ultrasound beam can be transmitted from the plurality of transducers of the transducer array 11 by using the high transmission voltage supplied from the HV power supply circuit 39 of the apparatus main body 2 during wired connection, which makes it possible to display a clear B-mode image of a deeper region of the subject under examination.

After that, in step S4 of FIG. 5, it is determined whether or not the examination using ultrasound waves has been completed, and in a case where it is determined that the examination has not yet been completed, the process returns to step S1, and processing of steps S1 and S3 is repeated, and in a case where it is determined that the examination has been completed, a series of processing ends.

As described above, by mounting the built-in battery 20 and the HV power supply circuit 21 each of which allows for a small mounting space within the ultrasound probe 1, the ultrasound probe 1 that is compact and has excellent portability is configured. Therefore, the operability of the ultrasound probe 1 is improved in a case where the ultrasound probe 1 and the apparatus main body 2 are connected via wireless connection, and a clearer ultrasound image can be acquired by supplying a higher transmission voltage than the transmission voltage during wireless connection from the HV power supply circuit 39 of the apparatus main body 2 to the transmission circuit 12 of the ultrasound probe 1 in a case where the ultrasound probe 1 and the apparatus main body 2 are connected via wired connection. That is, it is possible to achieve both improvement in operability of the ultrasound probe 1 during wireless connection and acquisition of an ultrasound image with high image quality during wired connection.

Further, a power voltage converted to, for example, about 5 V, which is higher than the output voltage of the built-in battery 20 of the ultrasound probe 1, is supplied to the system power supply circuit 22 of the ultrasound probe 1 by the bus power supply circuit 40 of the apparatus main body 2 during wired connection, so that it is possible to reduce the power loss while using the same system power supply circuit 22, and it is possible to suppress temperature rise inside the ultrasound probe 1.

Since the output voltage from the battery 38 is boosted to about 70 to 100 V and supplied to the transmission circuit 12 of the ultrasound probe 1 by the HV power supply circuit 39 of the apparatus main body 2 during wired connection, heat is generated from the HV power supply circuit 39. However, since the HV power supply circuit 39 is mounted inside the apparatus main body 2, the temperature rise caused by the heat generated by the HV power supply circuit 39 does not occur inside the ultrasound probe 1.

The surface temperature of the ultrasound probe 1 is limited to a temperature below predetermined safety standards. During wireless connection, the HV power supply circuit 21, which has a relatively low output voltage, is used in the ultrasound probe 1 so that the temperature rise inside the ultrasound probe 1 is suppressed while sacrificing the performance degradation of ultrasound image generation, and during wired connection, the transmission voltage is supplied from the HV power supply circuit 39, which has a relatively high output voltage, of the apparatus main body 2 to the transmission circuit 12 in the ultrasound probe 1 so that an ultrasound image with high image quality can be obtained while suppressing the temperature rise inside the ultrasound probe 1. As a result, both during wireless connection and during wired connection, the power consumption in the ultrasound probe 1 is suppressed, which enables prolonged operation of the ultrasound probe 1 using the built-in battery 20.

In addition, the probe control unit 18 of the ultrasound probe 1 can drive the reception circuit 13 in a low power consumption mode in order to suppress the power consumption in the ultrasound probe 1 in a case where the apparatus main body 2 is connected to the ultrasound probe 1 via wireless connection, and can also drive the reception circuit 13 in a low noise mode in order to improve the image quality of the ultrasound image to be generated, in a case where the apparatus main body 2 is connected to the ultrasound probe 1 via wired connection.

Further, the probe control unit 18 of the ultrasound probe 1 supplies the power voltage from the bus power supply circuit 40 of the apparatus main body 2 to the system power supply circuit 22 of the ultrasound probe 1 to supply the drive voltage from the system power supply circuit 22 to each circuit in the ultrasound probe 1 including the transmission circuit 12, the reception circuit 13, and the image generation unit 15 in a case where the apparatus main body 2 is connected to the ultrasound probe 1 via wired connection, thereby reducing the power loss inside the probe control unit 18, so that the image generation unit 15 can also generate the ultrasound image at a higher frame rate than the that during wireless connection.

The HV power supply circuit 21 of the ultrasound probe 1 can be configured to supply a variable transmission voltage to the transmission circuit 12, whereby the probe control unit 18 can supply the transmission circuit 12 with, for example, a transmission voltage corresponding to the depth of a region to be imaged from the HV power supply circuit 21 in a case where the apparatus main body 2 is connected to the ultrasound probe 1 via wireless connection.

Further, the HV power supply circuit 39 of the apparatus main body 2, which constitutes the external power supply circuit, can also be configured to supply the transmission circuit 12 with a variable transmission voltage having a voltage range wider than the transmission voltage supplied from the HV power supply circuit 21 of the ultrasound probe 1 during wireless connection in a case where the apparatus main body 2 is connected to the ultrasound probe 1 via wired connection. As a result, for example, in order to acquire a clear B-mode image of a deeper region of the subject under examination, a transmission voltage higher than that during wireless connection can be supplied to the transmission circuit 12, and a transmission voltage lower than that during wireless connection can also be supplied to the transmission circuit 12 in a case where ultrasound pulses are repeatedly transmitted, for example.

Embodiment 2

Figure 7:
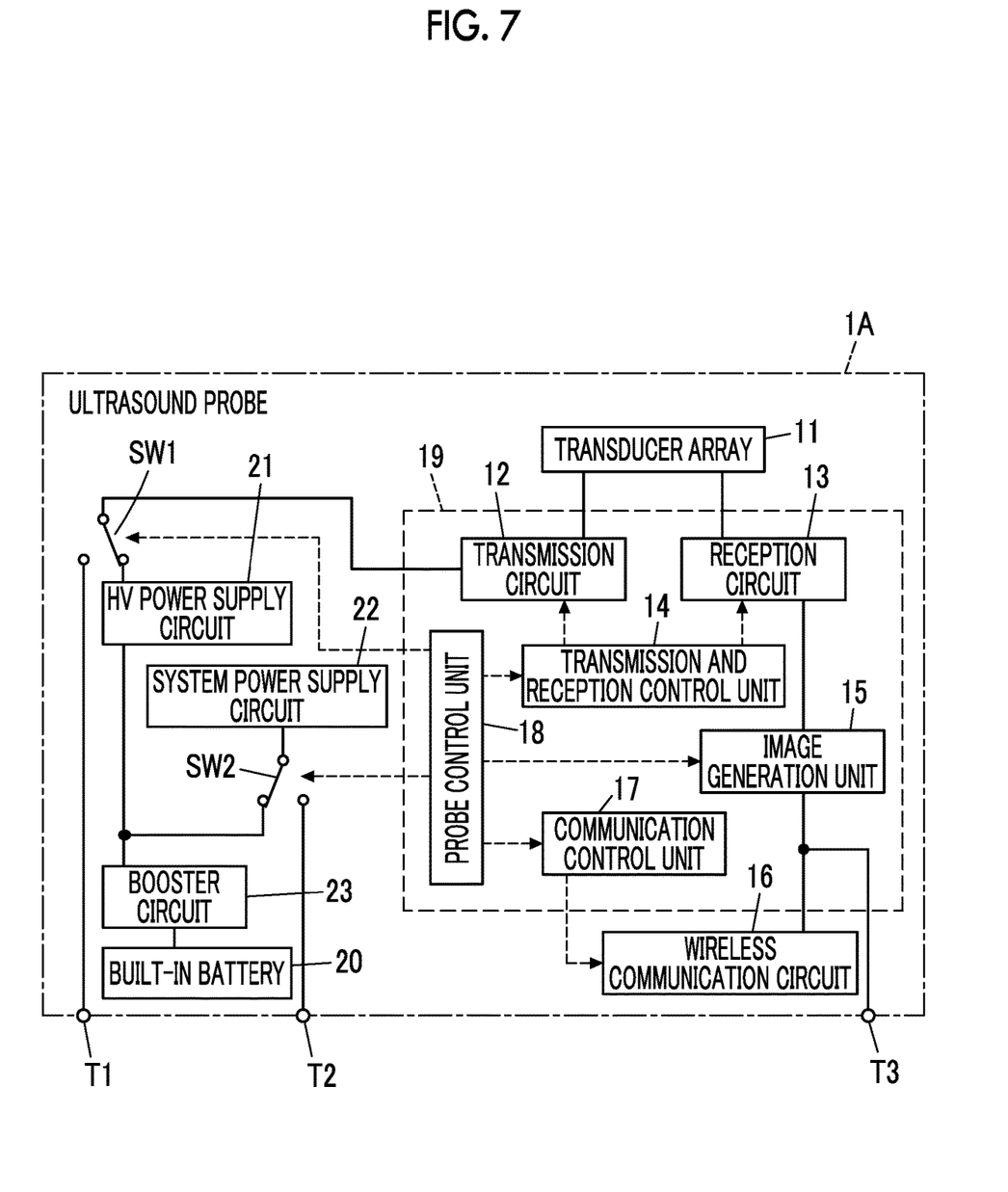
FIG. 7 is a block diagram showing a configuration of an ultrasound probe used in an ultrasound diagnostic apparatus according to Embodiment 2.

FIG. 7 shows a configuration of an ultrasound probe 1A used in an ultrasound diagnostic apparatus according to Embodiment 2 of the present invention. The ultrasound probe 1A is obtained by adding a booster circuit 23 to the ultrasound probe 1 used in the ultrasound diagnostic apparatus of Embodiment 1 shown in FIG. 1. The booster circuit 23 is connected to the built-in battery 20, and the HV power supply circuit 21 and the second changeover switch SW2 are connected to the booster circuit 23. Other configurations of the ultrasound probe 1A are the same as those of the ultrasound probe 1 shown in FIG. 1.

The booster circuit 23 boosts an output voltage of the built-in battery 20, such as 3.6 V to, for example, 5 V, 12 V, or the like, and is a circuit that has, for example, a boost converter configuration which does not use a transformer and that allows for a small mounting space within the ultrasound probe 1A.

In a case where the apparatus main body 2 shown in FIG. 1 is connected to the ultrasound probe 1A shown in FIG. 7 via wireless connection, the probe control unit 18 switches and controls the first changeover switch SW1 such that the HV power supply circuit 21 is connected to the transmission circuit 12, and switches and controls the second changeover switch SW2 such that the booster circuit 23 is connected to the system power supply circuit 22. As a result, the output voltage of the built-in battery 20 is once boosted by the booster circuit 23, the transmission voltage further boosted by the HV power supply circuit 21 is supplied to the transmission circuit 12, and the voltage boosted by the booster circuit 23 is stepped down by the system power supply circuit 22 and is supplied as the drive voltage to each circuit in the ultrasound probe 1A. Accordingly, it is possible to improve the conversion efficiency of the power voltage in the ultrasound probe 1A.

On the other hand, in a case where the apparatus main body 2 shown in FIG. 1 is connected to the ultrasound probe 1A shown in FIG. 7 via wired connection, the probe control unit 18 switches and controls the first changeover switch SW1 such that the connection terminal T1 is connected to the transmission circuit 12, and switches and controls the second changeover switch SW2 such that the connection terminal T2 is connected to the system power supply circuit 22. As a result, similarly to the ultrasound diagnostic apparatus of Embodiment 1, the power voltage boosted by the HV power supply circuit 39 of the apparatus main body 2 is supplied from the connection terminal T1 to the transmission circuit 12 via the first changeover switch SW1 without passing through the booster circuit 23 of the ultrasound probe 1A. In addition, a power voltage converted to, for example, about 5 V by the bus power supply circuit 40 of the apparatus main body 2 is supplied from the connection terminal T2 to the system power supply circuit 22 via the second changeover switch SW2, and the drive voltage is supplied from the system power supply circuit 22 to each circuit in the ultrasound probe 1A.

In Embodiments 1 and 2 described above, as the apparatus main body 2, a portable or handheld compact apparatus main body can be used, and a stationary apparatus main body can also be used. The apparatus main body 2 can also be configured to draw power from a commercial power source without incorporating the battery 38.

EXPLANATION OF REFERENCES

1, 1A: ultrasound probe
2: apparatus main body
11: transducer array
12: transmission circuit
13: reception circuit
14: transmission and reception control unit
15: image generation unit
16: wireless communication circuit
17: communication control unit
18: probe control unit
19: probe side processor
20: built-in battery
21: HV power supply circuit (in-probe power supply circuit)
22: system power supply circuit
23: booster circuit
31: wireless communication circuit
32: display control unit
33: monitor
34: communication control unit
35: main body control unit
36: input device
37: main body side processor
38: battery
39: HV power supply circuit (external power supply circuit)
40: bus power supply circuit (external power supply circuit)
41: amplification section
42: AD conversion section
43: beam former
44: signal processing section
45: DSC
46: image processing section
T1 to T6: connection terminal
SW1: first changeover switch
SW2: second changeover switch
C: cable.

What is claimed is:

1. An ultrasound diagnostic apparatus comprising:
   an apparatus main body; and
   an ultrasound probe that is used by switching between a wireless connection mode and a wired connection mode with respect to the apparatus main body,
   wherein
   the apparatus main body includes
      a main body-side first power supply circuit configured to generate a main body-side driving voltage, and
      a main body-side second power supply circuit configured to generate a main body-side transmission voltage higher than the main body-side driving voltage, and
   the ultrasound probe includes
      a transducer array,
      a built-in battery,
      a probe-side first power supply circuit configured to generate a probe-side driving voltage using an output voltage of the built-in battery,
      a probe-side second power supply circuit configured to boost the output voltage of the built-in battery to generate a probe-side transmission voltage higher than the probe-side driving voltage, and
      a probe side processor,
      the probe side processor being configured to
         in a case where the apparatus main body is connected to the ultrasound probe via wireless connection, receive the probe-side driving voltage generated by the probe-side first power supply circuit to operate, and cause an ultrasound wave to be transmitted toward a subject under examination by supplying the probe-side transmission voltage generated by the probe-side second power supply circuit to the transducer array, and
         in a case where the apparatus main body is connected to the ultrasound probe via wired connection, receive the main body-side driving voltage generated by the main body-side first power supply circuit to operate, and cause an ultrasound wave to be transmitted toward the subject under examination by supplying the main body-side transmission voltage generated by the main body-side second power supply circuit to the transducer array, and
         receive an ultrasound echo from the subject under examination and acquire a reception signal.

2. The ultrasound diagnostic apparatus according to claim 1,
   wherein the main body-side transmission voltage is higher than the probe-side transmission voltage.

3. The ultrasound diagnostic apparatus according to claim 1,
   wherein the probe side processor is configured to:
      perform the receiving of the ultrasound echo and the acquiring of the reception signal in a low power consumption mode in a case where the apparatus main body is connected to the ultrasound probe via wireless connection; and
      perform the receiving of the ultrasound echo and the acquiring of the reception signal in a low noise mode in a case where the apparatus main body is connected to the ultrasound probe via wired connection.

4. The ultrasound diagnostic apparatus according to claim 2,
   wherein the probe side processor is configured to:
      perform the receiving of the ultrasound echo and the acquiring of the reception signal in a low power consumption mode in a case where the apparatus main body is connected to the ultrasound probe via wireless connection; and
      perform the receiving of the ultrasound echo and the acquiring of the reception signal in a low noise mode in a case where the apparatus main body is connected to the ultrasound probe via wired connection.

5. The ultrasound diagnostic apparatus according to claim 1,
   wherein the probe side processor is configured to:
      generate an ultrasound image based on the reception signal; and
      generate the ultrasound image at a higher frame rate than a frame rate during wireless connection in a case where the apparatus main body is connected to the ultrasound probe via wired connection.

6. The ultrasound diagnostic apparatus according to claim 2,
   wherein the probe side processor is configured to:
      generate an ultrasound image based on the reception signal; and
      generate the ultrasound image at a higher frame rate than a frame rate during wireless connection in a case where the apparatus main body is connected to the ultrasound probe via wired connection.

7. The ultrasound diagnostic apparatus according to claim 3,
wherein the probe side processor is configured to:
generate an ultrasound image based on the reception signal; and
generate the ultrasound image at a higher frame rate than a frame rate during wireless connection in a case where the apparatus main body is connected to the ultrasound probe via wired connection.

8. The ultrasound diagnostic apparatus according to claim 1,
wherein the probe-side second power supply circuit generates a variable probe-side transmission voltage, and
the main body-side second power supply circuit generates a variable main body-side transmission voltage having a voltage range wider than a voltage range of the probe-side transmission voltage.

9. The ultrasound diagnostic apparatus according to claim 2,
wherein the probe-side second power supply circuit generates a variable probe-side transmission voltage, and
the main body-side second power supply circuit generates a variable main body-side transmission voltage having a voltage range wider than a voltage range of the probe-side transmission voltage.

10. The ultrasound diagnostic apparatus according to claim 3,
wherein the probe-side second power supply circuit generates a variable probe-side transmission voltage, and
the main body-side second power supply circuit generates a variable main body-side transmission voltage having a voltage range wider than a voltage range of the probe-side transmission voltage.

11. The ultrasound diagnostic apparatus according to claim 5,
wherein the probe-side second power supply circuit generates a variable probe-side transmission voltage, and
the main body-side second power supply circuit generates a variable main body-side transmission voltage having a voltage range wider than a voltage range of the probe-side transmission voltage.

12. A control method for an ultrasound diagnostic apparatus including an apparatus main body that includes a main body-side first power supply circuit configured to generate a main body-side driving voltage, and a main body-side second power supply circuit configured to generate a main body-side transmission voltage higher than the main body-side driving voltage, and an ultrasound probe that is used by switching between a wireless connection mode and a wired connection mode with respect to the apparatus main body and that includes a transducer array, a built-in battery, a probe-side first power supply circuit configured to generate a probe-side driving voltage using an output voltage of the built-in battery, a probe-side second power supply circuit configured to boost the output voltage of the built-in battery to generate a probe-side transmission voltage higher than the probe-side driving voltage, and a probe side processor, the control method comprising:
in a case where the apparatus main body is connected to the ultrasound probe via wireless connection, operating the probe side processor by supplying the probe-side driving voltage generated by the probe-side first power supply circuit to the probe side processor to cause an ultrasound wave to be transmitted toward a subject under examination by supplying the probe-side transmission voltage generated by the probe-side second power supply circuit to the transducer array;
in a case where the apparatus main body is connected to the ultrasound probe via wired connection, operating the probe side processor by supplying the main body-side driving voltage generated by the main body-side first power supply circuit to the probe side processor to cause an ultrasound wave to be transmitted toward the subject under examination by supplying the main body-side transmission voltage generated by the main body-side second power supply circuit to the transducer array; and
receiving an ultrasound echo from the subject under examination and acquire a reception signal.

13. The control method for an ultrasound diagnostic apparatus according to claim 12,
wherein the main body-side transmission voltage is higher than the probe-side transmission voltage.

14. The control method for an ultrasound diagnostic apparatus according to claim 12,
wherein the probe side processor is driven to receive an ultrasound echo and acquire a reception signal in a low power consumption mode in a case where the apparatus main body is connected to the ultrasound probe via wireless connection, and
the probe side processor is driven to receive an ultrasound echo and acquire a reception signal in a low noise mode in a case where the apparatus main body is connected to the ultrasound probe via wired connection.

15. The control method for an ultrasound diagnostic apparatus according to claim 12,
wherein an ultrasound image is generated by the probe side processor based on a reception signal at a higher frame rate than a frame rate during wireless connection.

16. The control method for an ultrasound diagnostic apparatus according to claim 12,
wherein a variable probe-side transmission voltage is supplied from the probe-side second power supply circuit to the probe side processor, and
a variable main body-side transmission voltage having a voltage range wider than a voltage range of the probe-side transmission voltage is supplied from the main body-side power supply circuit to the probe side processor.

* * * * *